United States Patent [19]

Bowman

[11] Patent Number: 5,439,008
[45] Date of Patent: Aug. 8, 1995

[54] INFANT REFLUX RESTRAINT APPARATUS

[76] Inventor: Karolen C. Bowman, P.O. Box 216, North Wilkesboro, N.C. 28659

[21] Appl. No.: 172,566

[22] Filed: Dec. 22, 1993

Related U.S. Application Data

[63] Continuation-in-part of Ser. No. 987,663, Dec. 9, 1992, Pat. No. 5,329,934.

[51] Int. Cl.$^6$ .......................... A61F 5/37; A61G 7/05; A47D 13/08
[52] U.S. Cl. ...................................... 128/875; 128/870; 128/846; 128/845; 5/424; 5/655
[58] Field of Search ............... 128/845, 846, 869, 870, 128/872, 873, 874, 875, 876; 5/494, 424, 655, 657, 900.5, 636, 640, 644

[56] References Cited

U.S. PATENT DOCUMENTS

| | | |
|---|---|---|
| Re. 24,377 | 10/1957 | Creelman . |
| 914,785 | 3/1909 | Boyce ............... 128/869 X |
| 1,061,275 | 5/1913 | Edmonds ............. 5/636 X |
| 1,386,652 | 8/1921 | Patton .................. 5/640 |
| 1,980,848 | 11/1934 | Cass . |
| 2,336,707 | 12/1943 | Thompson ............. 5/636 |
| 2,404,505 | 7/1946 | Knecht ............. 128/876 X |
| 2,451,007 | 10/1948 | White ............... 297/485 X |
| 2,456,898 | 12/1948 | Strandhagen . |
| 2,495,482 | 1/1950 | Robatz ............. 128/876 X |
| 2,758,595 | 8/1956 | Lovett . |
| 2,777,138 | 1/1957 | Gallagher . |
| 3,034,502 | 5/1962 | Lund . |
| 3,215,334 | 11/1965 | Tayman . |
| 3,327,330 | 6/1967 | McCullough ............ 5/636 X |
| 3,346,892 | 10/1967 | DuPriest ............... 5/636 X |
| 3,358,141 | 12/1967 | Hoffman et al. . |
| 3,369,548 | 2/1968 | Moore et al. . |
| 3,388,407 | 6/1968 | Harris . |
| 3,526,222 | 9/1970 | Dreibelbis . |
| 3,650,523 | 3/1972 | Darby, Jr. . |
| 3,828,377 | 8/1974 | Eary, Sr. . |
| 3,848,281 | 11/1974 | Mathews ............... 5/636 |
| 3,888,407 | 6/1975 | Harris ................. 5/622 X |
| 3,987,505 | 10/1976 | Hickey ................ 5/424 X |
| 4,027,869 | 6/1977 | Ruiz . |
| 4,030,719 | 6/1977 | Gabriele et al. . |
| 4,074,373 | 2/1978 | Garofalo ................ 5/640 |
| 4,108,168 | 8/1978 | Craig . |
| 4,205,669 | 6/1980 | Hamann . |
| 4,359,045 | 11/1982 | Cozzi .................. 401/5 |
| 4,383,713 | 5/1983 | Roston ................. 5/655 X |

(List continued on next page.)

FOREIGN PATENT DOCUMENTS 1449012  7/1966  France ..................... 5/655

Primary Examiner—Robert A. Hafer
Assistant Examiner—Brian E. Hanlon
Attorney, Agent, or Firm—Bell, Seltzer, Park & Gibson

[57] ABSTRACT

An infant reflux restraint apparatus according to the present invention preferably has a wedge-shaped support member for readily positioning an infant on a support surface to thereby support an infant in a reclined position. A pair of side strips are secured to the wedge-shaped support member and are positioned on an upper surface thereof. The pair of side strips are spaced-apart in a generally parallel relationship and a sufficient amount so that an infant can be positioned therebetween. Each of the pair of side strips also longitudinally extends along adjacent respective sides of the infant. The apparatus further preferably has a head support member connected to the wedge-shaped support member and positioned on an upper medial portion of the upper surface thereof for supporting the infant's head when reclined thereon. A reflux sling member detachably connects to the pair of side strips secured to the wedge-shaped support member and is positionally longitudinally aligned with the head support member for positioning the lower torso of the infant therein when reclined on the wedge-shaped support member.

3 Claims, 3 Drawing Sheets

U.S. PATENT DOCUMENTS

| | | | |
|---|---|---|---|
| 4,441,221 | 4/1984 | Ensle et al. | 5/655 X |
| 4,471,767 | 9/1984 | Guimond | 601/5 |
| 4,550,458 | 11/1985 | Fiore | 5/640 X |
| 4,617,691 | 10/1986 | Monti et al. | 5/636 X |
| 4,657,005 | 4/1987 | Williamson . | |
| 4,672,958 | 6/1987 | Garman | 128/846 |
| 4,693,212 | 9/1987 | Black . | |
| 4,731,890 | 3/1988 | Roberts | 5/636 X |
| 4,757,811 | 7/1988 | Clark . | |
| 4,802,244 | 2/1989 | McGath-Saleh | 5/494 X |
| 4,840,362 | 6/1989 | Bremer et al. . | |
| 4,854,305 | 8/1989 | Bremer . | |
| 4,858,625 | 8/1989 | Cramer . | |
| 4,862,535 | 9/1989 | Roberts | 5/655 |
| 4,911,105 | 3/1980 | Hocum . | |
| 4,911,106 | 3/1990 | Goodwin . | |
| 4,923,187 | 5/1990 | Mombrinie | 5/925 X |
| 4,989,286 | 2/1991 | Tucker . | |
| 5,027,833 | 7/1991 | Calkin . | |
| 5,028,925 | 5/1993 | Edlund . | |
| 5,044,026 | 9/1991 | Matthews | 5/644 |
| 5,056,533 | 10/1991 | Solano | 128/845 |
| 5,076,288 | 12/1991 | Millard et al. . | |
| 5,103,514 | 4/1992 | Leach | 5/655 X |
| 5,127,422 | 7/1992 | Colon | 5/555 X |
| 5,182,828 | 2/1993 | Alivizatos | 5/655 X |
| 5,207,478 | 5/1993 | Freese et al. | 5/655 X |
| 5,208,925 | 5/1993 | Edlund | 5/424 |

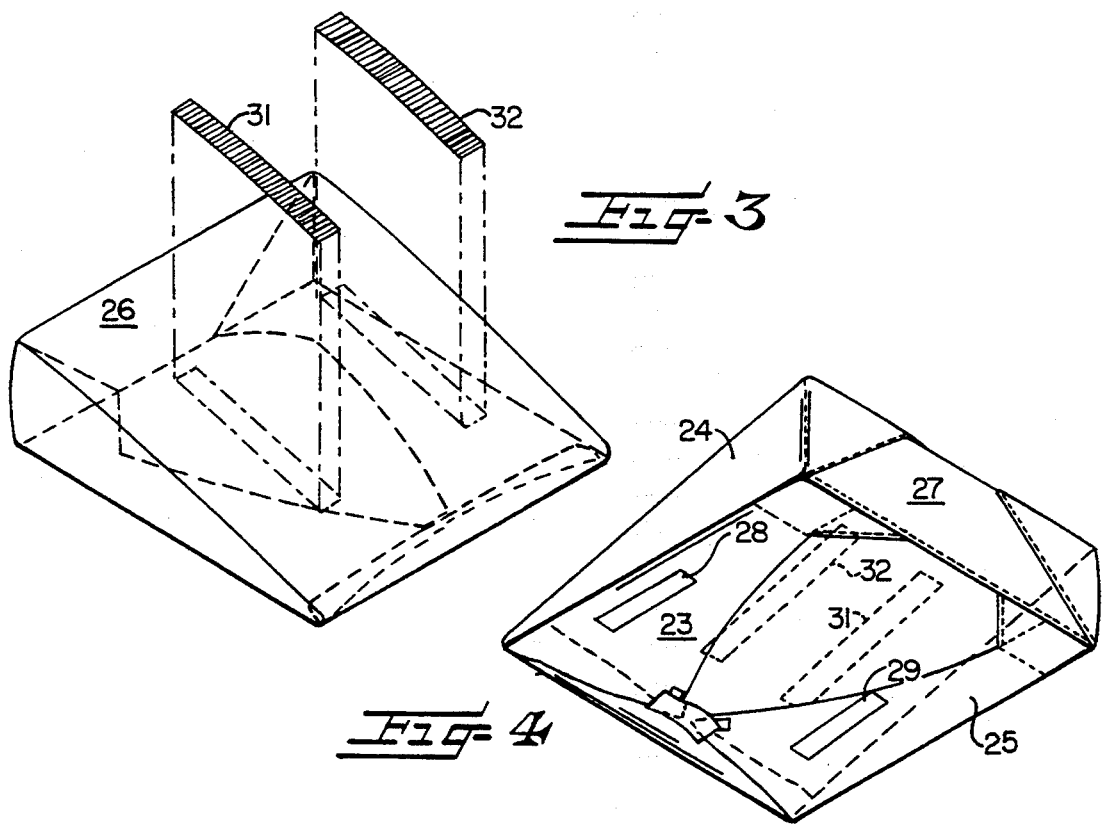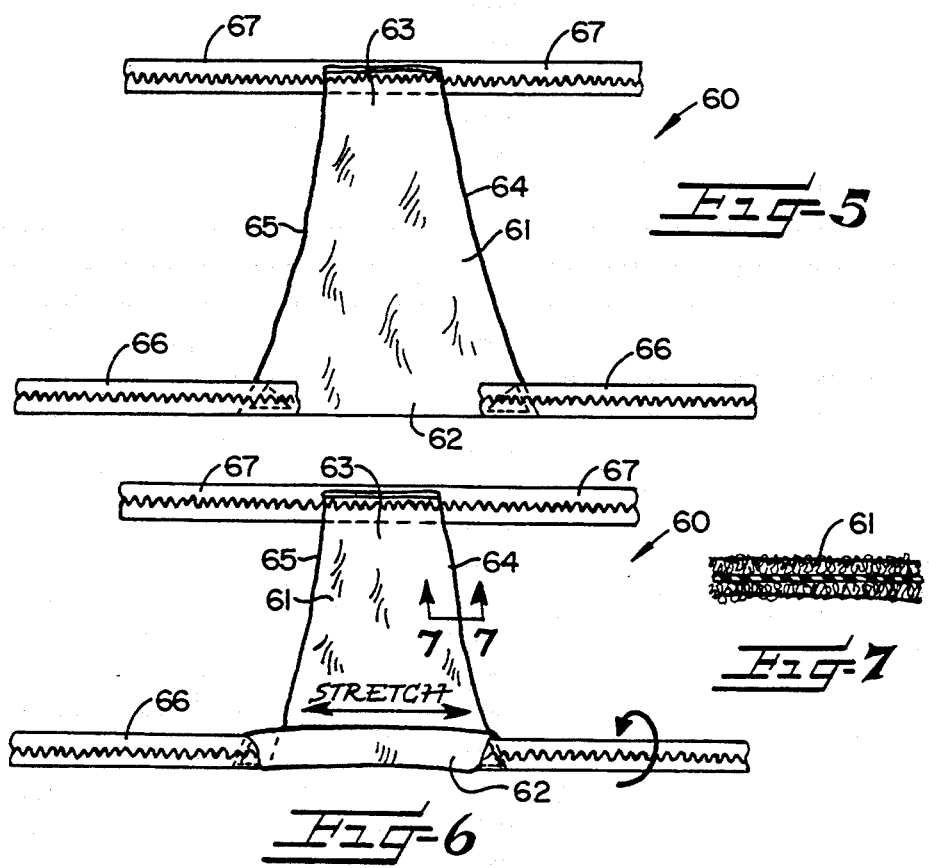

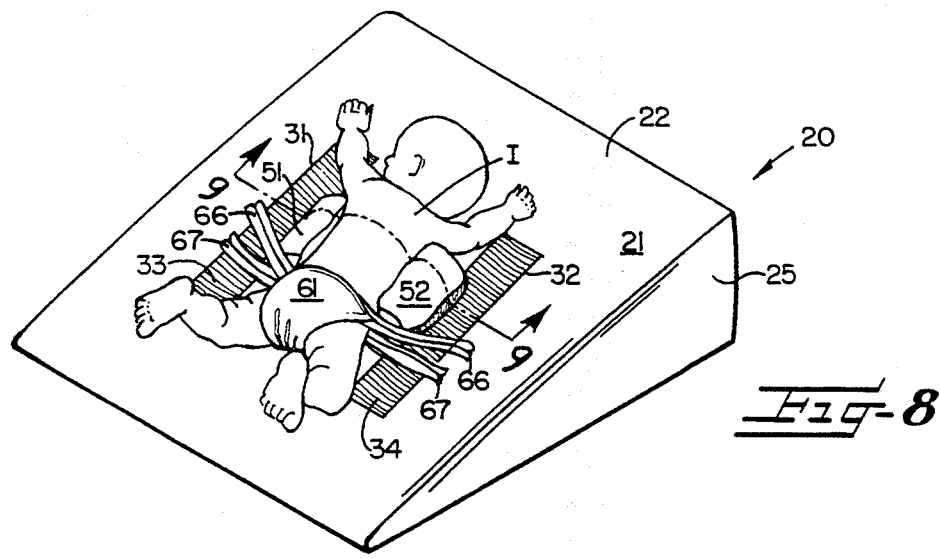
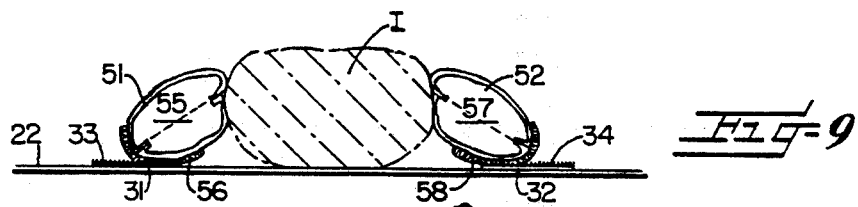
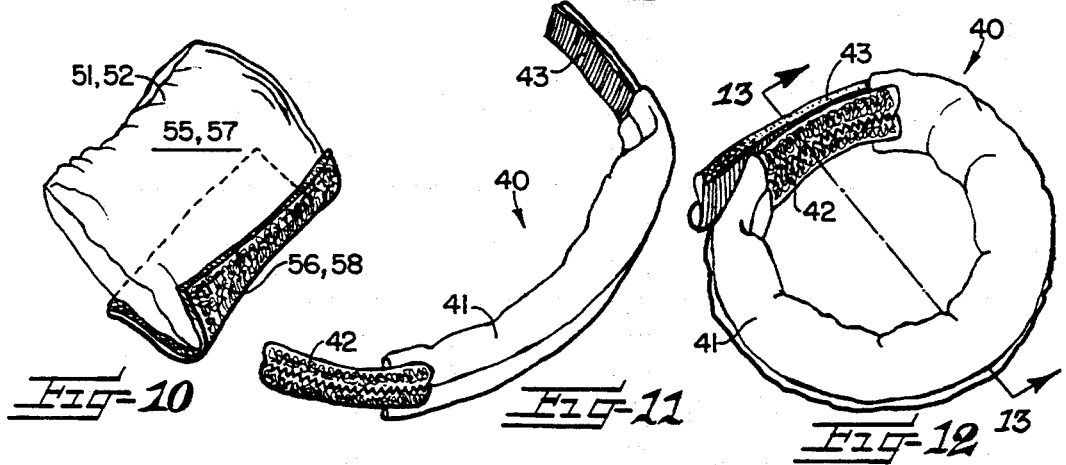
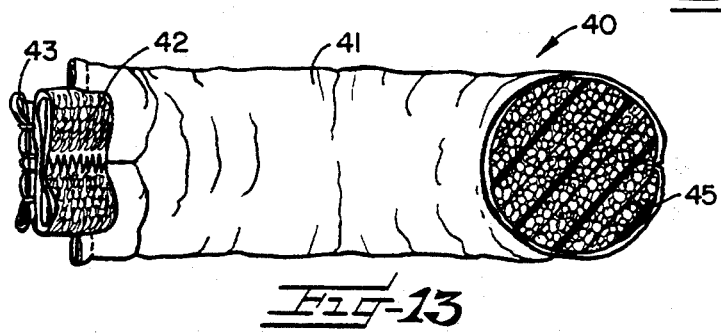

INFANT REFLUX RESTRAINT APPARATUS

RELATED APPLICATIONS

This application is a continuation-in-part of U.S. patent application Ser. No. 07/987,663 filed on Dec. 9, 1992, now U.S. Pat. No. 5,329,934.

FIELD OF INVENTION

The invention relates to an infant restraint apparatus and, more particularly, to an apparatus for restraining an infant to reduce problems associated with instances of gastroesophageal reflux.

BACKGROUND OF THE INVENTION

Physicians, and more particularly pediatricians, often suggest that an infant or a child be propped-up or inclined when both awake and asleep. An inclined posture often helps an infant to sleep during time of illness such as head colds or sinus infections. Various methods have been used to place the infant or child in a reclined position, including, for example, placing pillows underneath the infant to position the infant in the inclined position. Pillows, however, are typically very soft and assume the contour of the overlying infant. Consequently, there is a danger that the infant or child may suffocate if the child's face becomes directed toward the pillow. The flexibility of the pillows also may not provide the foundational strength required to support the infant in a predetermined position. For example, the infant may easily roll over or slide off the pillow.

Also, a recurring problem among particularly small infants, i.e., usually less than six months old, is Sudden Infant Death Syndrome ("SIDS"). These small infants die suddenly, often while in a crib, from what appears to be a type of suffocation. Some physicians have thought that SIDS may occur from pillows or blankets blocking air passages of the infant. Although the suffocation can occur from pillows, blankets, or the like positioned in the crib, other physicians also believe that gastroesophageal reflux causes the suffocation by fluid or particles blocking the air passages of the infant. The influence of gravity when an infant is in an inclined position is believed to aid the esophageal passage by reducing the regurgitation of stomach contents which may travel up the esophagus and block the infant's air passages. Instances of reflux are believed to be higher with premature infants and smaller infants because the esophageal passages are less tight and these type of infants generally have smaller stomachs.

Various devices, other than pillows, have been developed for positioning an infant in an inclined position. These conventional devices positionally adjust the angular attitude of the mattress in the infant's crib such as seen in U.S. Pat. No. 5,208,925 by Edlund entitled "*Sheet For Inclined Infant Mattress.*" These inclined mattress devices, however, are usually difficult to position and adjust. Slings or the like have been used with these devices and typically connect to the crib side rails or side walls. Another example of such a device may be seen in U.S. Pat. No. 4,471,767 by Guimond entitled "*Therapeutic Device For Positional Treatment For Gastroesophageal Reflux.*" These connections of the sling to the side rails or side walls, however, are also often difficult to adjust and can cause entanglement problems with the infant when moving its arms, legs, and head. Also, these prior devices provide little comfort or security particularly to small infants.

SUMMARY OF THE INVENTION

It is an object of the present invention to provide an infant reflux restraint apparatus that comfortably positions an infant in an inclined position to reduce problems associated with instances of gastroesophageal reflux. The infant reflux restraint apparatus according to the present invention provides a restraint apparatus that positionally supports an infant's head, lower torso, and sides so that an infant positioned thereon comfortably, portably, safely, and securely rests in the inclined position without the risk of entanglement problems with side rails or side walls.

More particularly, an infant reflux restraint apparatus according to the present invention preferably has a wedge-shaped support member for readily positioning an infant on a support surface to thereby support an infant in a reclined position. A pair of side strips are secured to the wedge-shaped support member and positioned on the upper surface thereof. The pair of side strips are spaced-apart in a generally parallel relationship and a sufficient amount so that an infant can be positioned therebetween. Each of the pair of side strips longitudinally extends along an adjacent respective side of an infant when positioned therebetween. The apparatus further has a head support member connected to the wedge-shaped support member and positioned on an upper medial portion of the upper surface thereof for supporting an infant's head when reclined on the wedge-shaped support member.

A reflux sling member detachably connects to the pair of side strips and is positionally longitudinally aligned with the head support member and adapted for positioning the lower torso of an infant therein when reclined on the wedge-shaped support member. The reflux sling member includes a torso support portion having first and second ends. The first end of the torso support portion preferably has a greater widthwise extent than the second end, respective side edges of the torso support portion converge from the greater widthwise extending first end toward the shorter widthwise extending second end, and a pair of sling straps connected to respective first and second ends of the torso support portion for detachably connecting to the pair of side strips secured to the wedge-shaped support member. The reflux sling member is adapted so that the second end strap thereof is positioned on an underside of the lower torso of an infant and connected to said pair of side strips, the torso support portion extends between the infant's legs and over the lower torso of an infant, and the first end strap detachably connects to the pair of side strips to thereby support the lower torso of an infant on the wedge-shaped support member.

DETAILED DESCRIPTION OF THE DRAWINGS

Some of the objects and advantages of the present invention having been stated, others will become apparent as the description proceeds when taken in conjunction with the accompanying drawings, in which:

FIG. 3 is an exploded top perspective view of an infant reflux wedge according to the present invention;

FIG. 4 is a bottom perspective view of an infant reflux wedge according to the present invention;

FIG. 5 is a top plan view of an infant reflux sling according to the present invention;

FIG. 6 is a top plan view of an infant reflux sling illustrating the positionally sizing adaptability thereof according to the present invention;

FIG. 7 is a cross-sectional fragmentary view of an infant reflux sling according to the present invention taken along line 7—7 of FIG. 6 and with parts broken away for clarity;

FIG. 8 is another perspective view of an infant reflux restraint apparatus according to the present invention;

FIG. 9 is a side cross-sectional view of an infant reflux restraint apparatus according to the present invention taken along line 9—9 of FIG. 8;

FIG. 10 is a perspective view of an infant side support device of an infant reflux restraint apparatus according to the present invention;

FIG. 11 is a perspective view of an infant head support device of an infant reflux restraint apparatus according to the present invention;

FIG. 12 is another perspective view of an infant head support device of an infant reflux restraint apparatus according to the present invention; and FIG. 13 is a fragmentary cross-sectional view of an infant head support device of an infant reflux restraint apparatus according to the present invention taken along line 13—13 of FIG. 12.

DETAILED DESCRIPTION OF ILLUSTRATED EMBODIMENTS

The present invention now will be described more fully hereinafter with reference to the accompanying drawings in which illustrated embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art. Like numbers refer to like elements throughout.

Figure 1:
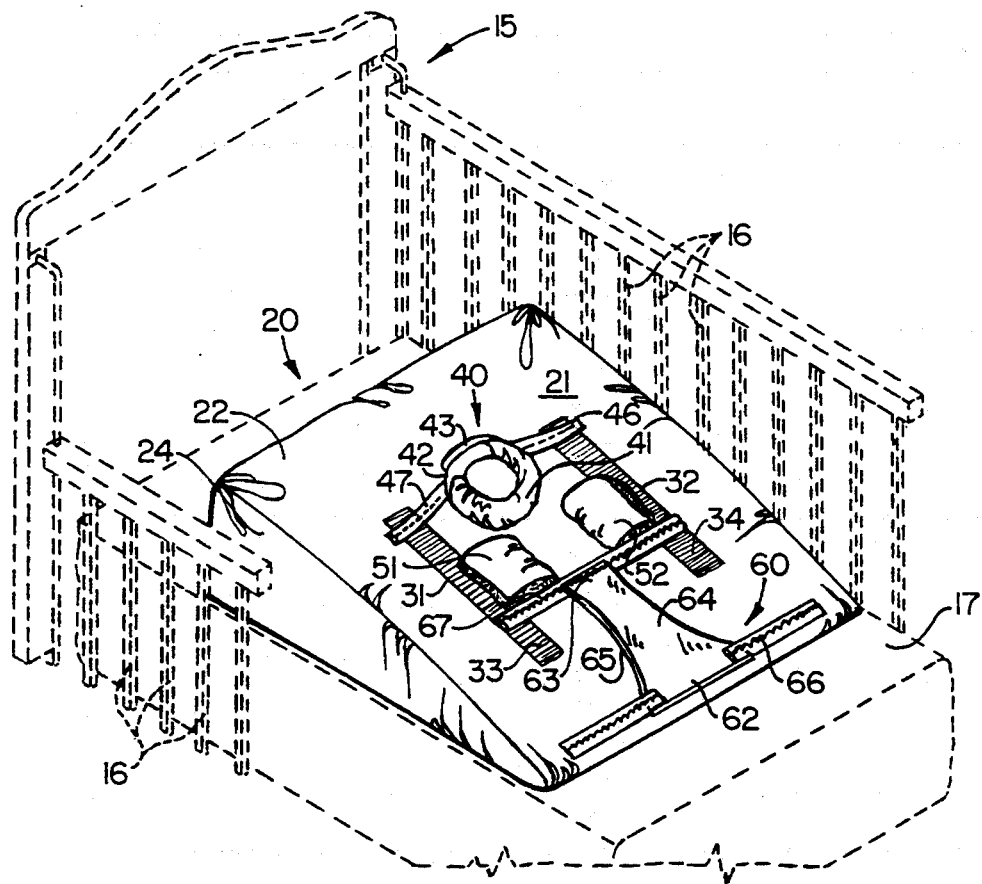
FIG. 1 is a perspective view of an infant reflux restraint apparatus according to the present invention positioned in an infant crib.
Figure 2:
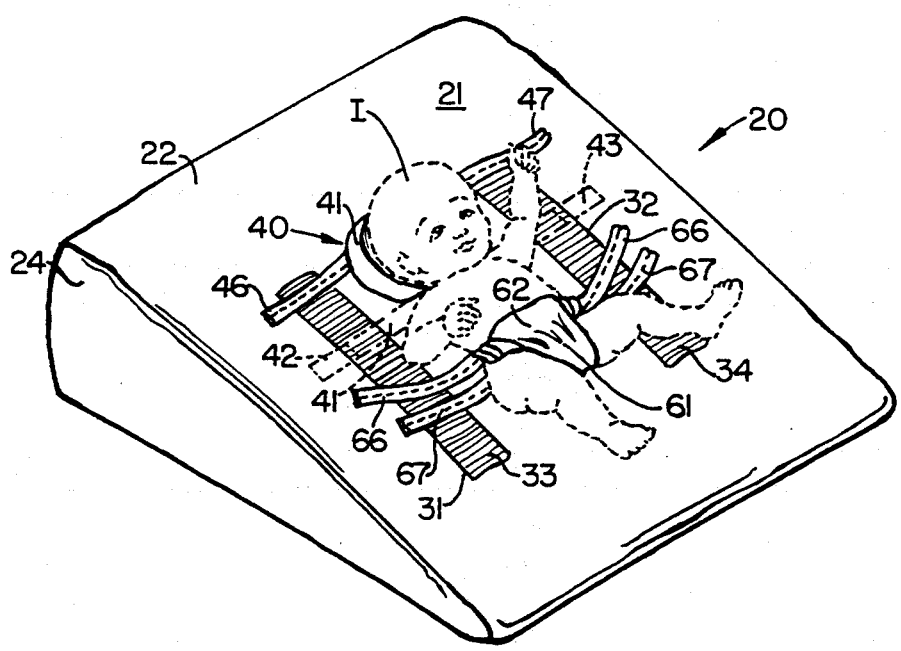
FIG. 2 is a perspective view of an infant reflux restraint apparatus according to the present invention illustrating an infant positionally restrained thereon.

FIGS. 1, 2, and 8 of the drawings illustrate perspective views of an infant reflux restraint apparatus 20 according to the present invention. As illustrated, the infant reflux restraint apparatus 20 preferably readily positions on a support surface such as a mattress 17 of an infant's crib 15 and comfortably supports an infant I thereon to thereby reduce reflux through the esophagus thereof and provides additional safety to the infant. The infant reflux restraint apparatus 20 preferably has a wedge-shaped support member 21 for readily positioning on a support surface 17 to thereby support an infant I thereon. It will also be apparent to those skilled in the art that another inclined support member having an inclined support surface such as an inclined mattress or the like may also be used according to the present invention.

The wedge-shaped support member 21 of the infant reflux restraint apparatus 20 preferably has rectangular-shaped upper and lower surfaces 22, 23 and triangular-shaped side surfaces 24, 25. In a preferred embodiment, the triangular-shaped side surfaces 24, 25 are each equilateral triangles having dimensions of about 25 inches by 25 inches by 7 inches. The upper surface 22 will therefore preferably be at an angle of about 20°–30° from the horizontal plane of the crib mattress 17 or the like. The size of the wedge-shaped support member 21 is such that it may readily be transported to various locations within the home or physician's office. The size also provides an easy fit into a typical infant crib and to comfortably cover the infant with a blanket, comforter, or the like. The wedge-shape provides protection against SIDS, other medical benefits of the inclined position, and enables a blanket covering the infant I positioned on the apparatus 20 to easily slide on and off the infant I.

A pair of side strips 31, 32 are secured to the rectangular-shaped upper surface 22 of the wedge-shaped support member 21. The pair of side strips 31, 32 are spaced-apart in a generally parallel relationship and a sufficient amount so that an infant I can be positioned therebetween. The distance between the pair of side strips 31, 32 is preferably about 10 inches. Each of the pair of side strips 31, 32 longitudinally extends along an adjacent respective side of the infant I. The side strips 31, 32 preferably each have a width of about 2-inches and a length of about 10 inches, and preferably have a fastener 33, 34 attached thereto. The fasteners 33, 34 attached to the pair of side strips 31, 32 are preferably either hooks or loops of Velcro-type fasteners (as best shown in FIGS. 8 and 9). In the illustrated embodiment, the pair of side strips 31, 32 are secured to a medial portion of the wedge-shaped support member 21 in the manner described below to thereby positionally align the infant I reclined thereon in a centered position for protective comfort to the infant I.

As best shown in FIGS. 3 and 4, the wedge-shaped support member 21 includes a wedge-shaped foam member 26 and a fabric casing 27 overlying and detachably connected to the wedge-shaped foam member 25 so that after use of the infant reflux restraint apparatus 20 the fabric casing 26 can be removed from the foam member 25 for easy cleaning and laundering of the fabric casing 26. The wedge-shaped foam member 25 preferably has a waterproof coating, such as a polyvinyl coating, to protect it from moisture from the infant I or the like. The fabric casing 26 is preferably formed of cotton, but may also be polyester, terry, cotton blends or other launderable materials. Also, the pair of side strips 31, 32 are preferably secured to the fabric casing 26 by stitching or the like. Although not preferable, the wedge-shaped support member 21 may further have fasteners 28, 29 secured to the lower surface 23 of the wedge-shaped support member and adapted to connect or secure the wedge-shaped support member 21 to a support surface such as the mattress 17 of an infant's crib The fasteners 28, 29 preferably include a pair of longitudinally extending fasteners 28, 29 spaced-apart in a generally parallel relationship and secured to the fabric casing 26, also by stitching or the like, to thereby detachably connect the wedge-shaped support member 21 to a support surface 17. These fasteners 28, 29 are also preferably hooks of Velcro-type fasteners. The hooks of Velcro-type fasteners may be received by mating loops of Velcro-type fasteners on a support surface or may be used to provide frictional resistance from slippage or the like when the hooks engage a fabric, i.e., polyester, or other material that cooperates with hooks.

A head support member 40 (as best shown in FIGS. 2 and 11-13) is preferably connected to the wedge-shaped support member 21 and positioned on an upper medial portion of the upper surface 22 for supporting the infant's head when reclined on the wedge-shaped support member 21. The head support member 40 preferably has an elongated padded body portion 41, i.e., of about 11 or 12 inches in length, and a pair of end straps 42, 43, i.e., of about 1 or 2 inches in length, connected to respective ends of the elongated body portion 41. The pair of end straps 42, 43 are adapted to connect to each other when the elongated body portion 41 has a generally circular shape (FIGS. 2 and 12) for comfortably positioning an infant's head thereon and are adapted to transversely connect to the pair of side strips 31, 32 when the elongated body portion transversely extends between the pair of side strips 31, 32 as best shown in FIGS. 2 (phantom view) and 11. A pair of extension straps 46, 47, i.e., of about 3 or 4 inches in length, also connect to the head support member 40 to thereby secure the head support member 40 to the pair of side strips 31, 32 when the elongated body portion 4 has a generally circular shape. The pair of end straps 42, 43 preferably have double-faced Velcro attached thereto by stitching or the like. The pair of extension straps 46, 47, in turn, also have Velcro-type fasteners attached thereto that matingly cooperate with the Velcro-type fasteners of the pair of end straps 42, 43 so that the head support member 40 can thereby be detachably secured to the pair of side strips 31, 32.

A reflux sling member 60 (as best shown in FIGS. 5–7) detachably connects to the pair of side strips 31, 32 secured to the wedge-shaped support member 21 and positionally aligns with the head support member 40 for positioning the lower torso of an infant I therein when reclined on the wedge-shaped support member 21. The reflux sling member 60 includes a torso support portion 61 preferably formed of a stretchable fabric (FIGS. 6 and 7), such as a polyester blend, Lycra, or the like, having first and second ends 62, 63. As illustrated in FIG. 6, the torso support portion 61 can readily be rolled from the first end 62 toward the second end 63 to thereby flexibly adjust the reflux sling member 60 for various size infants. The first end 62 of the torso support portion 61 preferably has a greater widthwise extent than the second end 63. The greater widthwise extending first end 62 provides coverage and support for the lower torso of an infant I. The shorter widthwise extending second end 63 provides coverage for the underside of the lower torso of an infant I and yet provides a comfortable area for an infant I to move its legs. Respective side edges 64, 65 of the torso support portion 61 also preferably continuously converge from the greater widthwise extending first end 62 toward the shorter widthwise extending second end 63.

First and second sling straps 66, 67 connect to respective first and second ends 62, 63 of the torso support portion 61 for detachably connecting to the pair of side strips 31, 32 positioned on the wedge-shaped support member 21. The first and second sling straps 66, 67 are preferably parallel to each other and each have opposite free end portions which extend beyond the torso support portion 61. As illustrated in FIGS. 2 and 8, the second end strap 67 is adapted to be transversely positioned on an underside of the lower torso of the infant I and detachably connect the pair of side strips 31, 32. The torso support portion 61 then preferably extends between an infant's legs, over an upperside of the lower torso of the infant I, and the first end strap 66 also transversely and detachably connects to the pair of side strips 31, 32 to thereby comfortably support the lower torso of the infant I on the wedge-shaped support member 21.

Each of the first and second end straps 66, 67 preferably has a fastener connected thereto. The fasteners are also preferably either the hooks or loops of Velcro-type fasteners or double-faced Velcro and matingly connect to the fasteners of the pair of side strips 31, 32. The opposite free end portions of each of the sling straps 66, 67 further preferably mount the fasteners of the pair of side strips 31, 32. These type fasteners enable the reflux sling member 60 to be easily and flexibly adjusted (see FIGS. 2 and 6) on the wedge-shaped support member 21 while also providing safe and secure positioning of an infant I thereon.

The infant reflux restraint apparatus 20 further preferably has a pair of side torso support members 51, 52 (as best shown in FIGS. 8–10). Each of the pair of side torso support members 51, 52 preferably has a body portion 55, 57 of about 5 or 6 inches in length and a pillow-type or block-type shape. A fastener 56, 58 is preferably attached by stitching or the like to the body portion 55, 57 as illustrated in FIG. 10. Each of the pair of side torso support members 51, 52 respectively connects to the pair of side strips 31, 32 by the fastener 56, 58 attached thereto and longitudinally extends along a respective side of an infant's torso for abuttingly engaging a side torso portion of an infant I when reclined on the wedge-support member 21. The fasteners 56, 58 are also either hooks or loops of Velcro-type fasteners. The side torso support members 51, 52 prevent an infant I reclined on the wedge-shaped support member 21 from laterally rolling off of the wedge-shaped support member 21.

In operation, and with reference to FIGS. 1, 2, and 8, the infant reflux restraint apparatus 20 may be portably and easily positioned within an infant's crib 15. Since the wedge-shaped support member 21 preferably has a width of about 25 inches, and a conventional crib mattress 17 has a width of about 45 inches, the size also provides an easy fit into an infant crib 15 and enables the parent or medical personnel to comfortably cover the infant with a blanket, comforter, or the like. The second sling strap 67 of the reflux sling member 60 can be connected to the pair of side strips 31, 32 with the torso support portion 61 and the first sling strap 66 in a generally flat position adjacent the wedge-shaped support member 21, as illustrated in FIG. 1. In this position, an infant I can be positioned between the pair of side strips 31, 32 with its head resting on the head support member 40 preferably when the head support member 40 is positioned in a generally circular shape as illustrated in FIG. 2. The lower torso of an infant I can then rest on the second sling strap 67 with the torso support portion 61 extending between the infant's legs. The first sling strap 66 can be lifted between the infant's legs and positioned so as to cover the lower torso portion of the infant I. The first sling strap 66 can then be transversely and detachably secured to the pair of side strips 31, 32 to thereby comfortably and securely support the infant I as illustrated in FIG. 2.

As illustrated in FIGS. 2 and 8, the infant I can either be positioned with its back abuttingly contacting the wedge-shaped support member 21 or the front of the infant I, i.e., stomach, positioned abuttingly contacting the wedge-shaped support member 21. When an infant I is reclined on the wedge-shaped support member 21 in the frontal position, the head support member 40 is preferably not used to thereby keep objects from and around the infant's face. The soft and firm wedge-shaped foam member 25 and the soft cotton fabric casing 26 provide padded comfort to an infant's head even if the head support member 40 is not used therewith.

The side torso support members 51, 52 can each be connected to the pair of side strips 31, 32 to abuttingly contact and support the side torso portions of the infant I (as best shown in FIG. 8). As also illustrated in FIG. 8, the first end strap 66 of the reflux sling member 60 preferably detachably connects to the pair of side strips 31, 32 adjacent respective lower end portions of the pair of side torso support members 51, 52. According to the present invention, however, the torso support portion 61 may extend and cover more of the lower torso of an infant I and the first end strap 66 may, in turn, also extend over each of the side torso support members 51, 52 and still detachably connect to the pair of side strips 31, 32.

The infant reflux restraint apparatus 20 according to the present invention thereby provides a restraint apparatus that positionally supports an infant's head, lower torso, and sides so that an infant positioned thereon comfortably, portably, safely, and securely rests in the inclined position. According to the present invention, other types of arm, leg, head, or torso restraint straps may also be detachably connected to the pair of side strips 31, 32 and adapted to secure arms, legs, head, or torso portions of an infant I to the wedge-shaped support member 21. An example of these restraint straps is illustrated in copending U.S. patent application Ser. No. 07/987,663 filed on Dec. 9, 1992 by the same inventor which is hereby incorporated herein by reference.

In the drawings and specification, there have been disclosed typical illustrative embodiments of the present invention, and although specific terms are employed, they are used in a generic and descriptive sense only and not for purposes of limitation, the scope on the invention being set forth in the following claims.

That which is claimed is:

1. An infant reflux restraint apparatus for readily positioning on a support surface such as in an infant crib and comfortably supporting an infant thereon to thereby reduce reflux by the infant through the esophagus thereof, the infant reflux restraint apparatus comprising:

a wedge-shaped support member for readily positioning an infant on a support surface to thereby support the infant in a reclined position;

a pair of side strips secured to said wedge-shaped support member and positioned on an upper surface thereof, said pair of side strips being spaced-apart in a generally parallel relationship and a sufficient amount so that an infant can be positioned therebetween and having each of said pair of side strips longitudinally extend along an adjacent respective side of an infant;

a head support member detachably connected to an upper end portion of said pair of side strips to thereby support an infant's head when reclined on said wedge-shaped support member, said head support member comprising an elongated padded body portion having a first end strap connected to a first end of said head support member, and having a second end strap connected to a second end of said head support member, said first and second end straps being detachably connected to each other when said elongated body portion has a generally circular shape for comfortably positioning an infant's head thereon and being arranged to transversely and detachably connect to said pair of side strips when said elongated body portion longitudinally extends between said pair of side strips; and a reflux sling member detachably connected to said pair of side strips and positionally longitudinally aligned with said head support member and adapted for positioning the lower torso of an infant therein when reclined on said wedge-shaped support member, said reflux sling member comprising a torso support portion having a first sling strap connected to a first end of said torso support portion, and a second sling strap connected to a second end of said torso support portion and extending outwardly therefrom, for detachably connecting to only a portion of said pair of side strips so that said second sling strap is adapted to be positioned on an underside of the lower torso of an infant and connect to only a portion of said pair of side strips, said torso support portion is adapted to extend between an infant's legs and over an upperside of the lower torso of an infant, and said first end strap is detachably connected to only a portion of said pair of side strips and thereby comfortably secure and support the lower torso of an infant on said wedge-shaped support member.

2. An infant reflux restraint apparatus as defined by claim 1, further comprising a pair of side torso support members, each of said pair of side torso support members respectively detachably connected to said pair of side strips and capable of longitudinally extending along respective sides of the infant's torso for abuttingly engaging side torso portions of the infant and thereby prevent the infant reclined on said wedge-shaped support member from laterally rolling off of said wedge-shaped support member.

3. An infant reflux restraint apparatus as defined by claim 2, wherein said first end strap detachably connects to said pair of side strips positionally adjacent respective lower end portions of said pair of side torso support members.

* * * * *